US012569356B2

(12) United States Patent
Paterson et al.

(10) Patent No.: US 12,569,356 B2
(45) Date of Patent: Mar. 10, 2026

(54) SURGICAL SPACER DEVICE FOR A JOINT

(71) Applicant: Limacorporate S.p.A., San Daniele del Friuli (IT)

(72) Inventors: Paul Paterson, West Falls, NY (US); Michele Pressacco, Martignacco (IT); Marco Dosso, Lumignacco (IT); Francesco Della Vedova, Cassacco (IT)

(73) Assignee: Limacorporate S.p.A., San Daniele del Friuli (IT)

( * ) Notice: Subject to any disclaimer, the term of this patent is extended or adjusted under 35 U.S.C. 154(b) by 292 days.

(21) Appl. No.: 18/024,710

(22) PCT Filed: Sep. 8, 2021

(86) PCT No.: PCT/EP2021/074717
§ 371 (c)(1),
(2) Date: Mar. 3, 2023

(87) PCT Pub. No.: WO2022/053519
PCT Pub. Date: Mar. 17, 2022

(65) Prior Publication Data
US 2023/0310179 A1 Oct. 5, 2023

(30) Foreign Application Priority Data

Sep. 10, 2020 (IT) ........................ 102020000021403

(51) Int. Cl.
*A61B 17/15* (2006.01)
*A61B 17/02* (2006.01)
(Continued)

(52) U.S. Cl.
CPC .......... *A61F 2/4612* (2013.01); *A61B 17/025* (2013.01); *A61F 2/4081* (2013.01); (Continued)

(58) Field of Classification Search
CPC ........ A61B 17/025; A61B 2017/00477; A61B 2017/564; A61F 2/40; A61F 2/4081; A61F 2/4612
See application file for complete search history.

(56) References Cited

U.S. PATENT DOCUMENTS

2008/0046084 A1 2/2008 Sledge
2009/0164017 A1 6/2009 Sommerich
(Continued)

FOREIGN PATENT DOCUMENTS

WO 2010/017307 A1 2/2010

OTHER PUBLICATIONS

International Search Report dated Oct. 27, 2021, issued in connection with PCT/EP2021/074717.
(Continued)

*Primary Examiner* — Samuel S Hanna
(74) *Attorney, Agent, or Firm* — Nixon Peabody LLP

(57) ABSTRACT
The present invention relates to a surgical spacer device (100) for a joint, comprising a substantially cylindrical or truncated-cone-shaped main body (101), internally hollow and configured for insertion in a distracted joint (1, 2); the main body (101) comprising: a first terminal surface (102) substantially flat and configured to abut onto a first bone portion (1) of the joint (1, 2); a second terminal surface (103) substantially annular and configured to abut onto a second bone surface (2) of the joint (1, 2) opposite the first bone portion (1), the second terminal surface (103) having a first opening (10) for access to the second bone portion (2); at least one lateral element (104) configured for maintaining a three-dimensional spaced structure between the first terminal surface (102) and the second terminal surface (103), the at least one lateral element (104) defining a second opening (20) configured for allowing a lateral access inside the main
(Continued)

body (101) and further an access to the second bone portion (2) through the first opening (10).

19 Claims, 8 Drawing Sheets

(51) Int. Cl.
*A61F 2/40*          (2006.01)
*A61F 2/46*          (2006.01)
*A61B 17/00*          (2006.01)
*A61B 17/56*          (2006.01)

(52) U.S. Cl.
CPC ............... *A61B 2017/00477* (2013.01); *A61B 2017/00876* (2013.01); *A61B 2017/564* (2013.01)

(56)                    References Cited

U.S. PATENT DOCUMENTS

| | | | |
|---|---|---|---|
| 2014/0121467 | A1 | 5/2014 | Vayser et al. |
| 2016/0143744 | A1* | 5/2016 | Bojarski ............... A61F 2/3804 623/20.35 |
| 2017/0239062 | A1 | 8/2017 | Williams |
| 2019/0167280 | A1* | 6/2019 | Wozencroft ......... A61B 17/175 |
| 2019/0216615 | A1 | 7/2019 | Paterson et al. |

OTHER PUBLICATIONS

International Preliminary Report on Patentability dated Dec. 16, 2022, issued in connection with PCT/EP2021/074717.

* cited by examiner

SMALL (a)     (b)     (c)

SURGICAL SPACER DEVICE FOR A JOINT

CROSS-REFERENCE TO RELATED APPLICATIONS

This application is a national phase of PCT/EP2021/074717, filed Sep. 8, 2021, and claims priority to Italian Patent Application No. 102020000021403, filed Sep. 10, 2020, the entire contents of both of which are hereby incorporated by reference.

FIELD OF APPLICATION

The present invention relates to a surgical spacer device for a joint. In general, the invention relates to an instrument which can be used in the field of surgery.

The invention is particularly useful in surgical operations of implantation of shoulder prostheses with different types of glenoid components; the following description is made with reference to this specific field of application in order to simplify the explanation thereof.

In general, it is not to exclude that the present invention can be applied in other types of surgical operations, such as surgical operations for the hip, knee, spinal column, etc. in order to maintain opposite ends of joints spaced apart.

PRIOR ART

In the field of shoulder prostheses, the usage of prostheses, typically modular prostheses consisting of a plurality of elements which can be combined with each other in order to obtain a reverse or anatomical prosthesis, and possibly in order to convert the prosthesis from anatomical to reverse, is already widespread.

Some commonly used shoulder prostheses provide the usage of a glenoid anchor, which is inserted in a hole previously obtained substantially at the center of the glenoid cavity. In case of an anatomical prosthesis, a polyethylene insert is typically fixed on the glenoid anchor, while, in case of a reverse prothesis, a convex glenoid joint component, called glenosphere, is typically fixed on the glenoid anchor.

In some types of surgical operations for implanting shoulder prosthesis, it is provided to perform a trans-humeral hole in the humeral head which extends in medial-lateral direction, and it is provided to maintain a gleno-humeral clearance between the humeral head and the glenoid cavity of the scapula, so as to access and perform the surgical operation and the implantation.

For this purpose, it is known to provide a retractor instrument insertable by a deltopectoral incision in order to maintain a space between the humeral head and the glenoid cavity free, in which a bone machining instrument is to be inserted.

An example of a retractor instrument is a simple surgical forceps, whose operation effectiveness is however clearly low.

Document US2019216615 (A1) refers to a specific retractor surgical instrument for implanting a glenoid component of a shoulder prosthesis. Such retractor surgical instrument has a first annular-shaped element which abuts onto a humeral head in order to allow the access through a trans-humeral hole, and a second element which abuts onto the coracoid process in order to maintain the glenoid cavity free, being substantially U-shaped and enclosing on a bottom side the coracoid process.

An emerging difficulty is to distract the gleno-humeral joint in a stable and accurate manner, so as to allow the surgeon to proceed with the implantation of the prosthetic components.

In the prior art, there are in fact problems for maintaining the positional stability of the gleno-humeral joint once distracted, with the risk of suddenly seeing the space available to the surgeon reduced and to damage the patient's anatomy, in particular nerves.

An object of the present invention is to provide a surgical device having structural and functional characteristics such as to overcome drawbacks of the prior art.

A further object of the present invention is to allow a stable and accurate maintenance of the position of the distracted joint during operations of prosthesis implantations.

A further object of the present invention is to allow a better visibility and access to the joint area for the surgeon during operations of prosthesis implantations.

SUMMARY OF THE INVENTION

The solution idea underlying the present invention is to provide a surgical spacer device configured to enter a distracted joint, maintaining it in this way for the duration of the operation, being in particular able to fit in the patient's anatomy, for example of a glenoid and of a resected humerus.

Advantageously, the insertion of the surgical spacer device forms the space necessary to guarantee visibility of the joint, and moreover the possibility of inserting further machining instruments mainly, but not only, for the glenoid area.

Based on such solution idea, it is provided a surgical spacer device for a joint, comprising a substantially cylindrical or truncated-cone-shaped main body, internally hollow and configured for insertion in a distracted joint. The main body comprising a first terminal surface substantially flat and configured to abut onto a first bone portion of the joint; a second terminal surface substantially annular and configured to abut onto a second bone surface of the joint opposite the first bone portion, the second terminal surface having a first opening for access to the second bone portion; at least one lateral element configured for maintaining a three-dimensional spaced structure between the first terminal surface and the second terminal surface, at least one lateral element defining a second opening configured for allowing a lateral access inside the main body and further an access to the second bone portion through the first opening.

Thereby, the same tensions, which are present in the distracted joint, maintain interposed the surgical spacer device, whose stability is guaranteed without any need for external personnel to maintain it in position.

Thus, advantageously, it becomes possible to maintain the position of the joint in a stable and accurate manner during operations of prosthesis implantation.

Furthermore, advantageously, visibility and access to the joint area are improved for the surgeon who operates during the operations of prosthesis implantation.

Preferably, the first terminal surface and the second terminal surface of the surgical spacer device are not parallel to each other but sloped for giving a wedge shape in the portion diametrically opposite the second opening. Advantageously, the insertion of the main body in the distracted joint is thereby eased.

Preferably, the first terminal surface of the main body further provides a hole, advantageously configured for passage of instruments or anchors from and to the first bone portion.

Furthermore, preferably, in the surgical spacer device according to the present invention, the main body is divided into two portions, along the coronal plane; advantageously, by allowing the opening of the main body in two body halves, the extraction of the surgical spacer device according to the present invention is eased, once the final implant is placed.

Furthermore, preferably, in the surgical spacer device according to the present invention, the main body can be associated with one or more substantially flat modular shims, adapted to increase an overall thickness in height and to adjust, in particular increase, a distraction quantity of the joint based on the operational requirements.

Advantageously, the surgical spacer device according to a preferred embodiment of the present invention is configured for insertion in a gleno-humeral distracted joint, and the first opening is sized to surround a glenoid cavity and to allow bone processing and implantation of prosthesis' glenoid components.

Further features and advantages of the invention will emerge from the following detailed description, provided for illustrative and non-limiting purposes, and from the claims which form an integral part of the present description.

4

In different figures, similar elements will be indicated by similar reference numbers.

DETAILED DESCRIPTION

Figure 1:
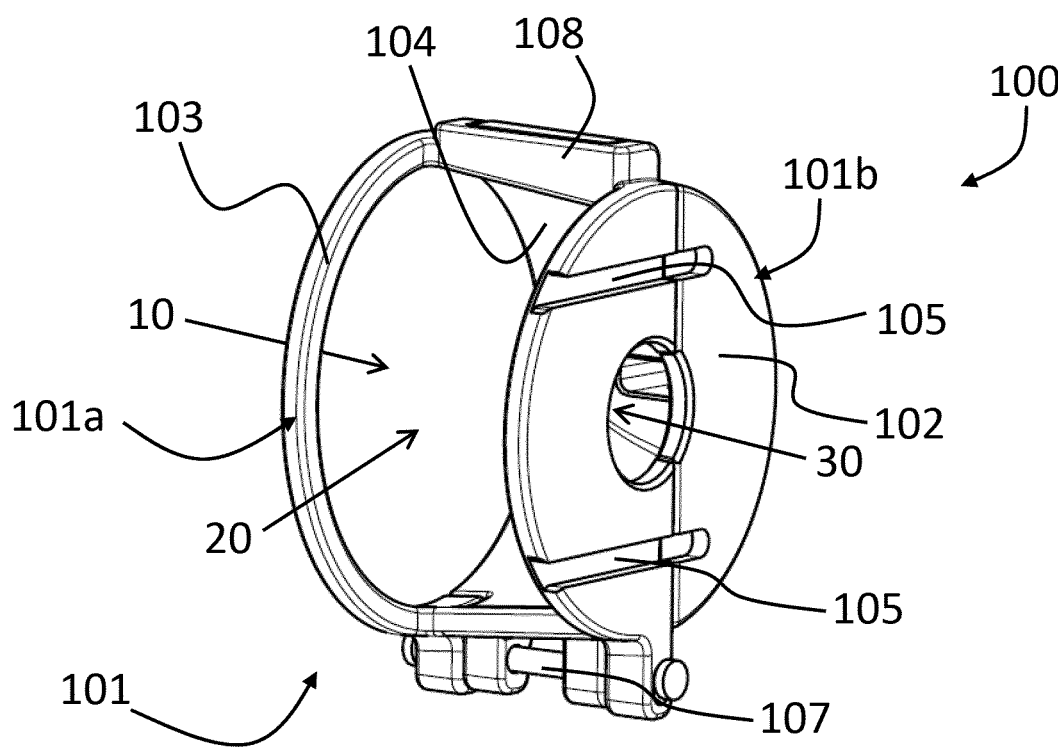
FIG. 1 shows a prospective view of one embodiment of a surgical spacer device according to the present invention.

FIG. 1 shows a prospective view of an embodiment of a surgical spacer device 100 according to the present invention.

The surgical spacer device 100 comprises a main body 101, substantially cylindrical or truncated-cone-shaped and internally hollow.

As will be further described, the main body can be made in two versions, based on needs, monolithic or openable and therefore divided into two halves.

In the embodiment exemplified in FIG. 1, the main body 101 is not monolithical but is openable in a first half body 101a and in a second half body 101b, rotatable around a hinge or pintle 107 and maintained closed by a closure 108, which will be described in the following.

The main body 101, in ways which will be further described, is configured for insertion in a distracted joint.

The main body 101 comprises a first terminal surface 102 substantially flat and configured to abut onto a first bone portion of the joint.

The main body 101 further comprises a second terminal surface 103 substantially annular and configured to abut onto a second bone portion of the joint, which is opposite the first bone portion.

The second terminal surface 103, as it can be seen, comprises a substantially annular closed-loop element. In other words, the second terminal surface 103 has a closed crown-like shape, which is adapted to abut onto the second bone portion of the joint. In particular, the shape of the second terminal surface 103 is configured to distribute pressure as evenly as possible on the second bone portion of the joint.

The second terminal surface 103 has a first opening 10 for access to the second bone portion, in ways which will be further described.

The main body 101 further comprises at least one lateral element 104, configured for maintaining a three-dimensional spaced structure of the main body 101 between the first terminal surface 102 and the second terminal surface 103.

In this embodiment, the at least one lateral element 104 is divided between the first half body 101a and the second half body 101b, which form the main body 101.

The lateral element 104 defines a second opening 20 which gives access to the hollow inside of the main body 101. Thus, the second opening 20 is configured to allow a lateral access inside the main body 101, and further to allow an access to the second bone portion, at the second terminal surface 103 through the first access opening 10.

In other words, in the "frontal" area with respect to the configuration in use, the surgical spacer device 100 has an opening at the lateral element 104, that is the second opening 20, which has the purpose of allowing the surgeon to view the joint space and insertion of the instruments necessary for machining the bone end, for example the glenoid, for the subsequent implantation of a prosthesis component.

In particular, in this embodiment, the first half body 101a comprises respective first portions of the first terminal surface 102 and of the second terminal surface 103, and further comprises a respective first portion including the second opening 20 of the at least one lateral element 104. On the other end, the second half body 101b comprises respective second portions of the first terminal surface 102 and of the second terminal surface 103, and further comprises a respective second portion of the at least one lateral element 104 diametrically opposite the second opening 20.

In general, the at least one lateral element 104 has a thickness and/or circumferential extension adapted to maintain the first terminal surface 102 and the second terminal surface 103 at a predetermined distance.

Looking at the main body 101 of the surgical spacer device 100 with different eyes, it can be said that the first terminal surface 102 is maintained at a predetermined distance from the second substantially annular terminal surface 103, by small columns or at least one junction wall. The overall wall resulting from such columns or junction wall is in particular extended for more than the half of the circumference of the ring of the second terminal surface 103.

Furthermore, as said, the planes to which the first terminal surface 102 and of the second substantially annular terminal surface 103 belong, are slightly convergent, so as to give a wedge shape in the portion diametrically opposite the second opening 20.

Preferably, the first terminal surface 102 further has a hole 30 configured for passage of instruments or anchors from the first bone portion, in ways which will be further described.

Preferably, the second opening 20 circumferentially occupies an angular sector greater than 90°, preferably greater than 135°, more preferably greater than 160°, of the lateral element 104 in order to allow a wide access to the joint area involved by the operation.

Preferably, furthermore, the second opening 20 substantially occupies the whole thickness in height available between the first terminal surface 102 and the second terminal surface 103.

Preferably, yet, the second substantially annular terminal surface 103 has a circular crown extension substantially equal to a wall thickness of the main body 101, thus maximizing the access to the bone area of the joint.

In particular, such angular sector and/or height and/or thickness are defined based on technical considerations, as a compromise between ease of access and mechanical resistance withstanding loads to which the surgical spacer device is subjected.

Figure 2:
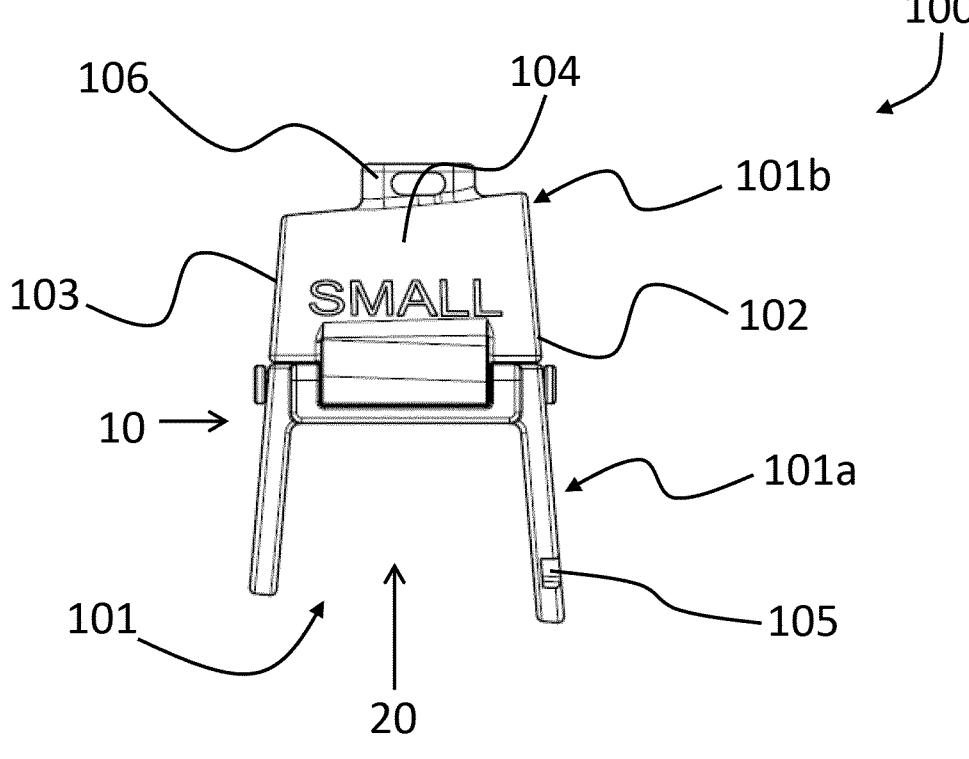
FIG. 2 shows an upper view of the surgical spacer device of FIG. 1.

FIG. 2 shows an upper view of the surgical spacer device 100.

As visible, preferably, the first terminal surface 102 and the second terminal surface 103 are not parallel to each other, but are slightly sloped to partially reduce a thickness in height of the main body 101 in a portion diametrically opposite the second opening 20, in particular in the portion identified by the second half body 101b. Thereby, a wedge shape is provided to the main body 101, which, it is reminded, is openable in the first half body 101a and in the second half body 101b. Such wedge shape is thinner in the portion diametrically opposite the second opening 20 of the main body 101, so as to ease the insertion thereof in a distracted joint.

The cone or wedge shape of the main body 101, in the Antero/Posterior plane with respect to the configuration in use, eases the progressive insertion of the surgical spacer device 100 in the joint, for example in a gleno-humeral joint.

Preferably, the surgical spacer device 100 is provided in different sizes, in order to guarantee a correct fitting on the specific anatomy of the patient.

Figure 3:
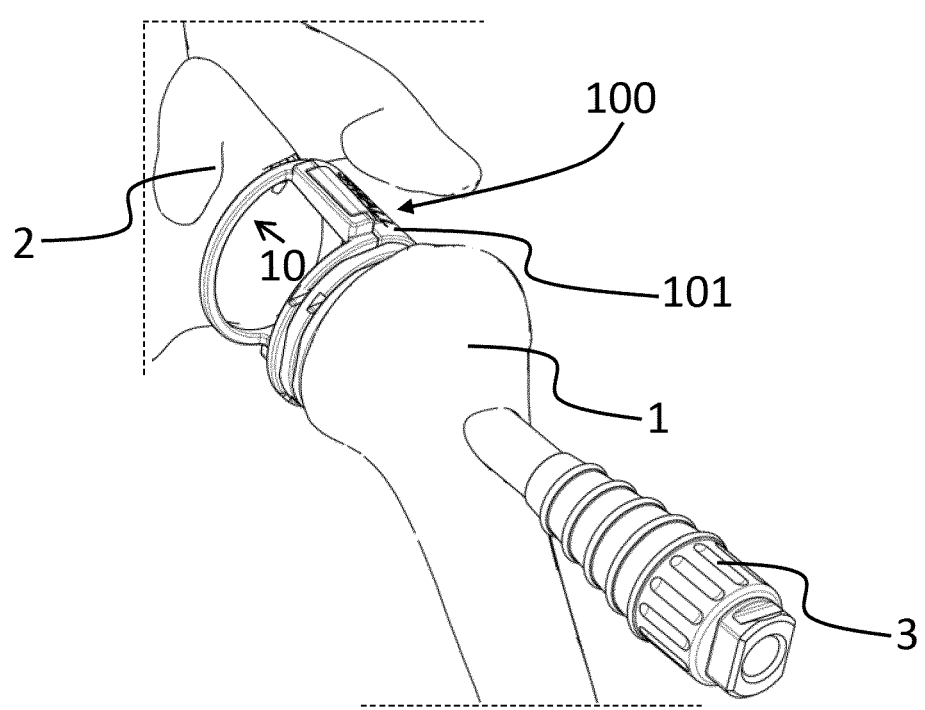
FIG. 3 shows a prospective view of a surgical spacer device according to the present invention, inserted into an anatomy and further associated with a surgical instrument.

FIG. 3 shows a prospective view of the surgical spacer device 100 inserted in an anatomy 1, 2 and further associated with a surgical instrument 3.

As said, the main body 101 is configured for insertion in a distracted joint. In this example, the surgical spacer device 100 is inserted in a gleno-humeral distracted joint, wherein the first bone portion 1 is humeral and the second bone portion 2 is glenoidal.

As visible, the first opening 10 is preferably sized to surround a glenoid cavity of the portion 2, so as to allow bone processing and implantation of prosthesis' glenoid components, passing through the main body 101.

Preferably, as described above, the first terminal surface 102 has the hole 30 (not visible in the figure) which is configured for passage of instruments 3 or anchors from the first bone portion 1.

In addition, the hole 30 has also the function to stabilize the relative movement between the surgical spacer device 100 and the humerus 1.

A particular aim of the surgical spacer device 100 is to distract the gleno-humeral joint 1, 2 being able to adapt both to the glenoid anatomy 2 and to one of the resected humerus 1 thanks to its shape. Thanks to the conical taper which characterizes the main body 101 in the Antero/Posterior plane, the surgical spacer device 100, which is provided in several sizes, can be easily positioned in the joint and its progressive insertion creates the space necessary to guarantee visibility of the joint, in addition to the possibility of inserting further machining instruments mainly, but not only, for the glenoid area 2.

The advantageous geometry of the surgical spacer device 100 both on the Antero/Posterior and the Medial/Lateral planes makes it so that the tensions present in the joint ensure the stability thereof without any need for external personnel to maintain it in position.

Figure 4:
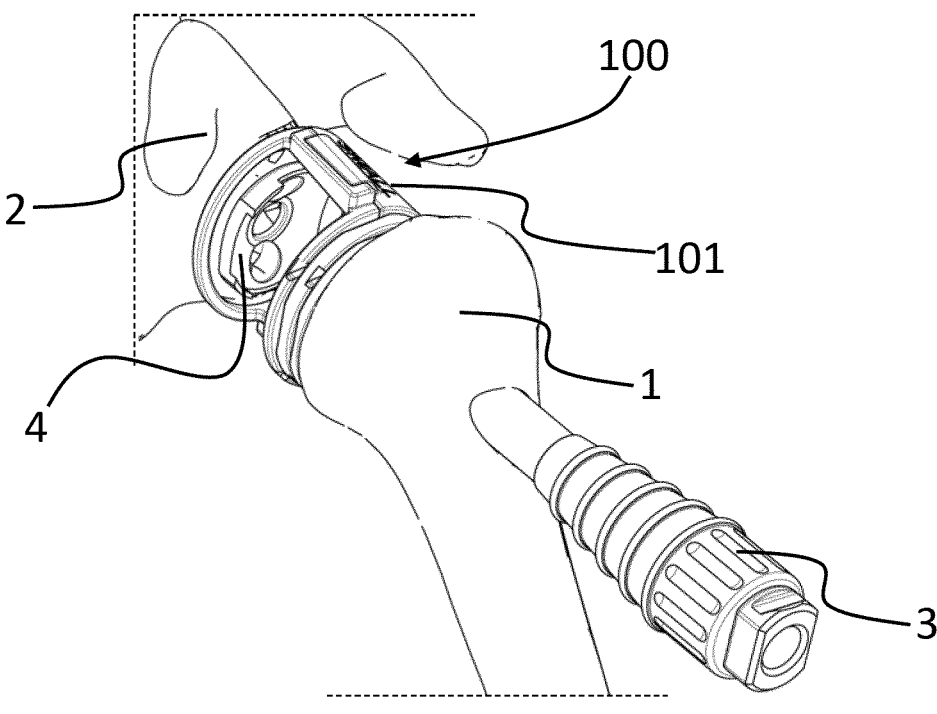
FIG. 4 shows the view of FIG. 3 to which a glenoid component of a shoulder prosthesis inserted through the surgical spacer device is added.

FIG. 4 shows the view of FIG. 3, to which a glenoid component 4 of a shoulder prosthesis is added, inserted passing through the surgical spacer device 100. In particular, the glenoid component 4 of the shoulder prosthesis is inserted through the second opening 20 of the main body 101, previously described.

As described, the glenoid side of the surgical spacer device 100 has a second terminal surface 103 substantially annular and such that it can surround the glenoid cavity, thus guaranteeing the possibility of using instruments necessary for machining of the glena for subsequent implantation of a glenoid prosthesis.

Figure 5:
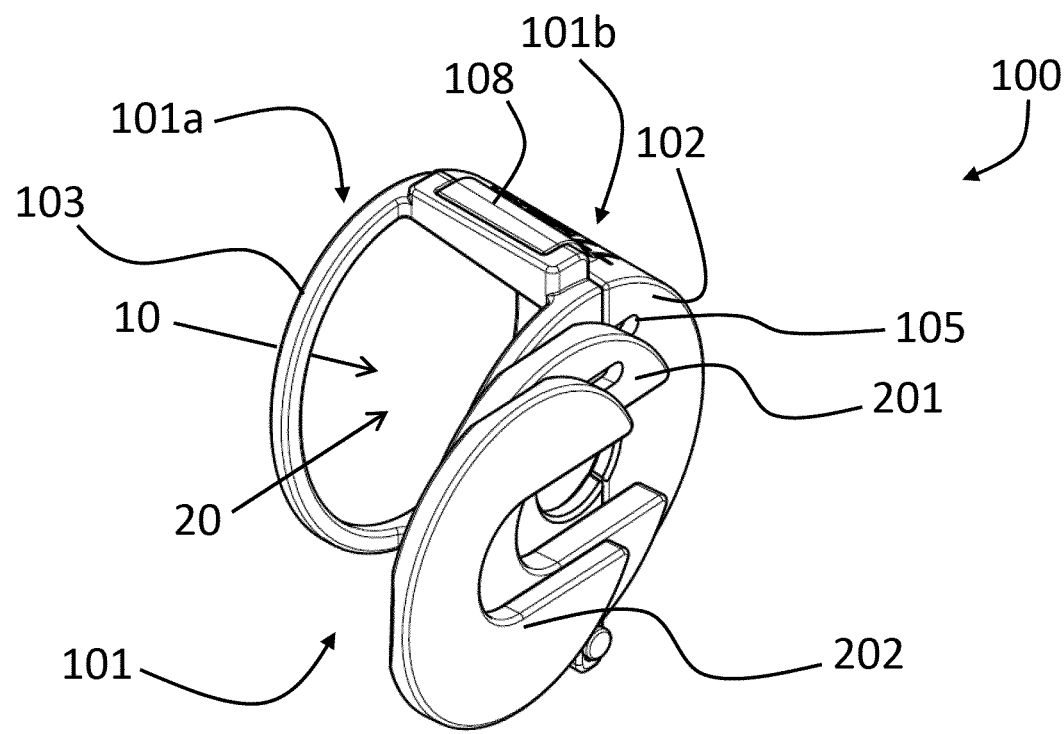
FIG. 5 shows a prospective view of a further embodiment of a surgical spacer device according to the present invention.

FIG. 5 shows a prospective view of a further embodiment of the surgical spacer device 100.

The surgical spacer device 100 may further comprise one or more modular shims 201, 202 substantially flat and associated with the main body 101 at the first terminal surface 102.

These modular shims 201 and 202 are adapted to increase an overall thickness in height of the main body 101 of the surgical spacer device 100, so as to increase a distraction quantity of the joint.

Figure 6:
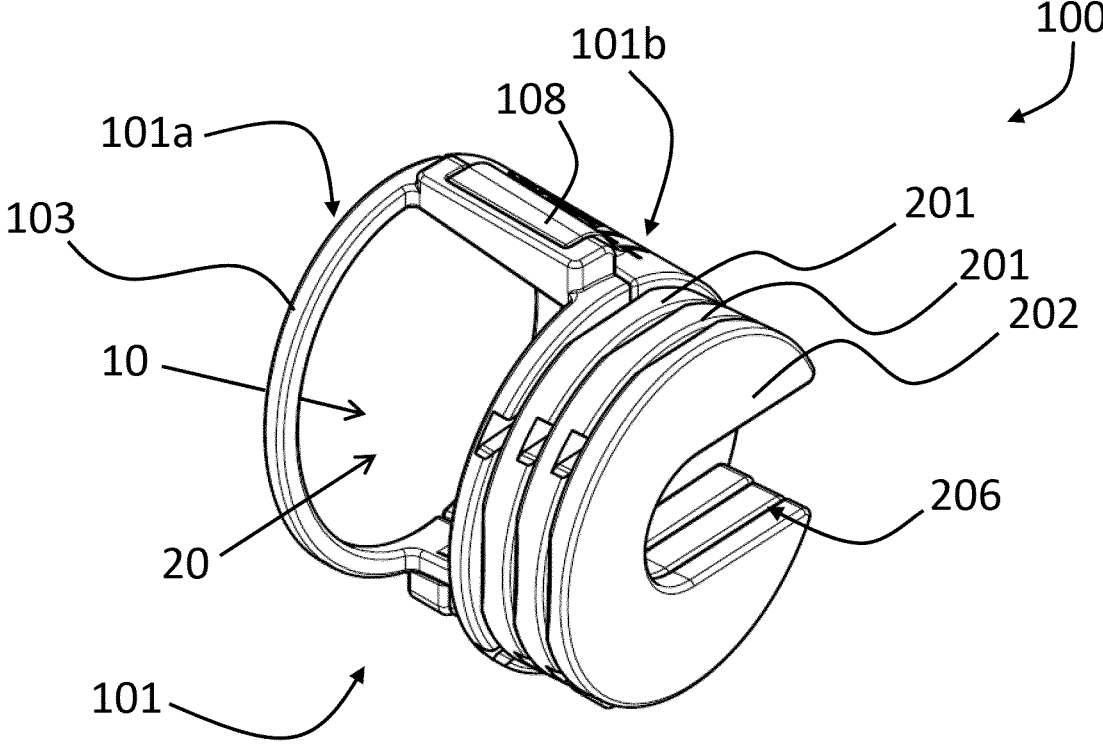
FIG. 6 shows the view of FIG. 5 in which all modular shims are installed in final position.

FIG. 6 shows the view of FIG. 5 in which all two modular shims 201 and one terminal modular shim 202 are installed in final position.

As it will be further described, the modular shims 201 and 202 comprise one central slit or cut-out 206 which allows the insertion thereof when in the hole 30 of the surgical spacer device 100 is already inserted any element, being it an instrument or an anchor.

Thanks to the central slit 206, the modular shims 201 and 202 can be inserted prior to positioning the surgical spacer device 100 in the joint, or even after this step if the achieved tension is not such as to allow maintenance of the surgical spacer device 100 in the correct position.

Preferably, the modular shims 201 and 202 have thicknesses different from each other; in a non-limiting example, the terminal modular shim 202 has a thickness lower than the other modular shims.

Figure 7:
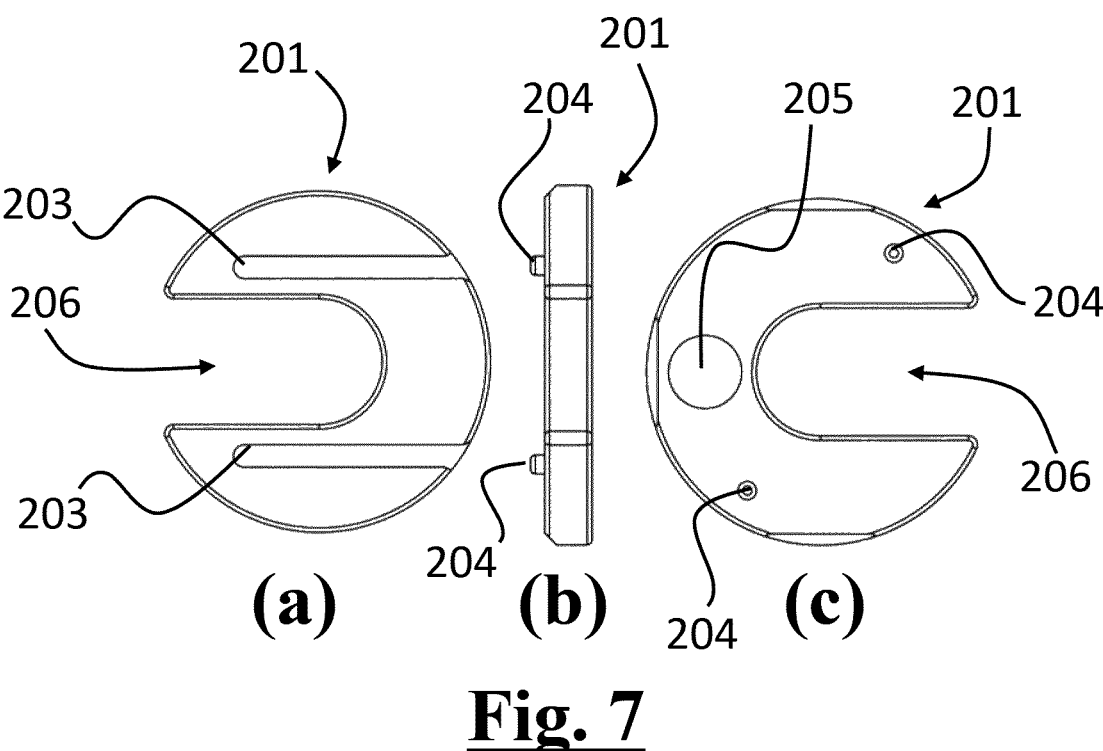
FIG. 7 shows a lateral view, a rear view, a medial view of an embodiment of modular shim of a surgical spacer device according to the present invention.

FIG. 7 respectively shows a lateral view (a), a rear view (b) and a medial view (c) of a modular shim 201.

Preferably, the modular shims 201 comprise respective grooves 203 and respective guide pins 204 on opposite faces.

The already-described first terminal surface 102 preferably comprises respective grooves 105, and the grooves 203 or 105 and the guide pins 204 are configured to modularly guide the subsequent insertion of the one or more modular shims 201.

Preferably, the respective grooves 203 are open on one side at the second opening 20 of the lateral element 104.

Preferably, the respective grooves 203 are parallel to each other, while the respective guide pins 204 are offset to each other with respect to the grooves 203, so as to sequentially engage the respective grooves 203 and as to improve guidance during the insertion of the modular shims 201.

As will be appreciated by a person skilled in the art, in an example of the terminal modular shim 202, only the guide pins 204 could be provided, without providing grooves 203, so as to offer a terminal surface in contact with the anatomy which is substantially smooth.

As previously described, further modular shims 201 and/or 202 can be added on the humeral side, in order to modify the original height of the surgical spacer device 100, thus guaranteeing greater joint distraction.

Preferably, the modular shims 201 and/or 202 comprise magnetic coupling means 205, such as a button magnet, configured for maintaining a stable contact between each other and, globally, with the main body 101. In other words, the magnet 205 guarantees the stable coupling of the modular assembly of the surgical spacer device 100 once obtained the desired positioning in the anatomy.

In general, the one or more modular shims 201 and/or 202, being substantially C-shaped with respective central cut-outs 206, are configured for surrounding instruments 3 or anchors, applied to the bone portion 2 at the first terminal surface 102.

Figure 8:
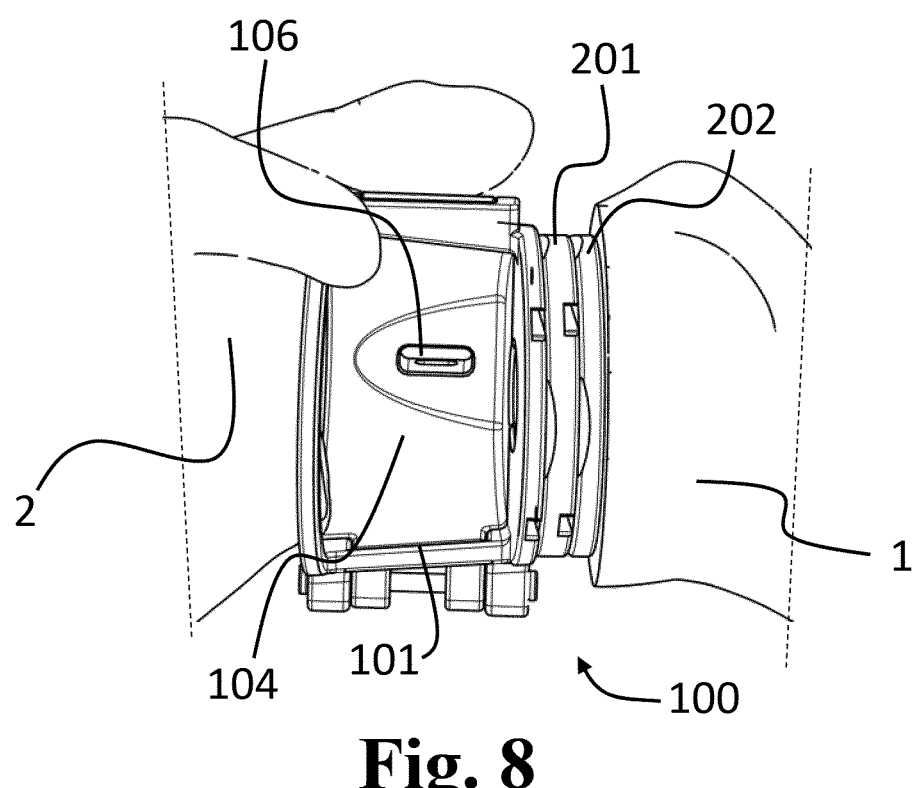
FIG. 8 shows a frontal schematic view of the surgical spacer device of FIG. 6 inserted in an anatomy.

FIG. 8 shows a lateral schematic view of the surgical spacer device 100 inserted in an anatomy of a distracted gleno-humeral joint 1, 2.

As visible, preferably, the main body 101 further internally comprises hooking means 106, on the lateral element 104 in a position opposite the second opening 20.

Such hooking means 106 are configured for removably coupling with a handle (not represented, described in the following) for insertion of the surgical spacer device 100 in the distracted joint.

Figure 9:
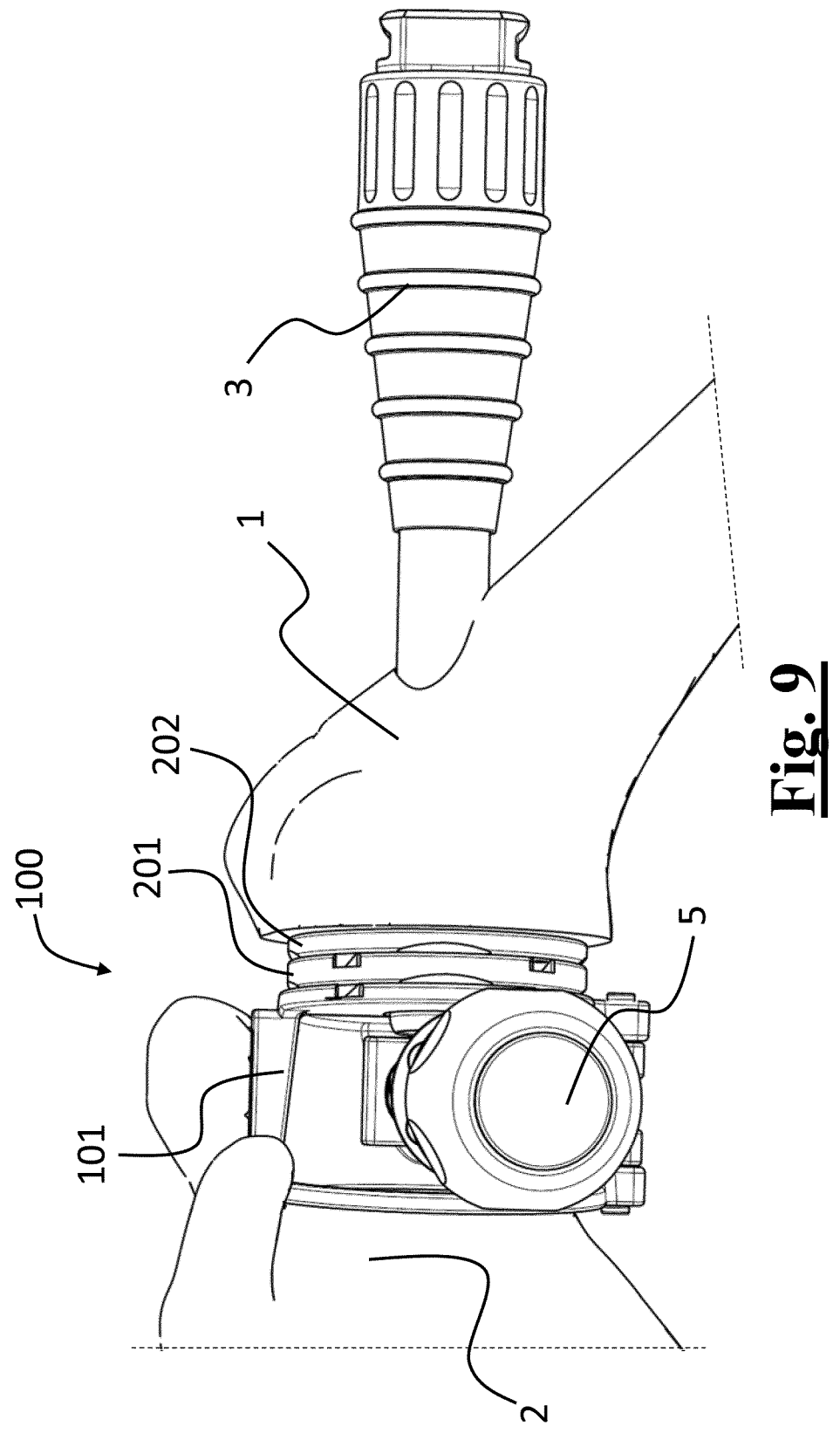
FIG. 9 shows a frontal schematic view of the surgical spacer device of FIG. 8, further associated with surgical instruments.

FIG. 9 shows a frontal schematic view of the surgical spacer device 100, further associated with surgical instruments 3 and 5.

The surgical spacer device 100 can be positioned in the gleno-humeral space 1, 2 manually or using a specific handle 5 which hooks with the hooking means 106 in order to avoid undesired unhooking thereof during the maneuvers.

After the insertion thereof, the handle 5, if present, is removed and it is evaluated if the tension reached in the distracted joint 1, 2 guarantees stability of the surgical spacer device 100 and correct accessibility and visibility of the anatomical elements.

If the tension is not enough, the need to add one or more modular shims 201, 202 is evaluated.

Thanks to the insertion of the surgical spacer device 100, it is possible to maintain in a stable and accurate manner the position of the joint 1, 2 during operations of prosthesis implantations.

Furthermore, by the surgical spacer device 100 provided with a hollow main body 101 and a first specific opening 10 and second specific opening 20, the visibility and access to the joint area 1, 2 are improved during operations of prosthesis implantations.

Figures 10, 11:
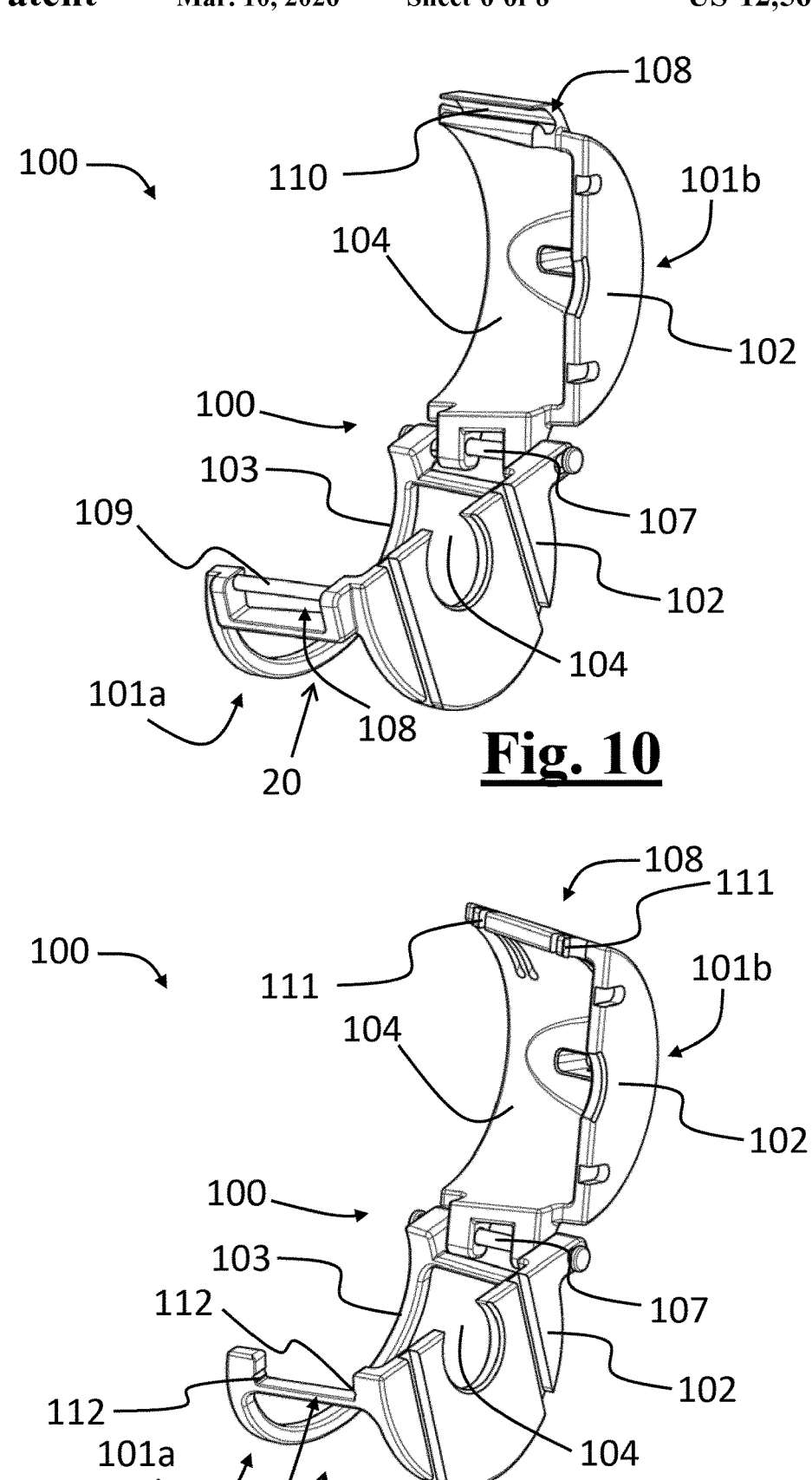
FIG. 10 shows a prospective view of a further embodiment of a surgical spacer device according to the present invention, in open configuration.
FIG. 11 shows a prospective view of still a further embodiment of a surgical spacer device according to the present invention, in open configuration.

FIG. 10 shows a prospective view of a further embodiment of a surgical spacer device 100 in open configuration.

As already described, the main body 101 is openable in a first half body 101a and in a second half body 101b. The first half body 101a comprises respective first portions of the first terminal surface 102 and of the second terminal surface 103, and then comprises a respective first portion of the at least one lateral element 104 including the second opening 20. The second half body 101b comprises respective second portions of the first terminal surface 102 and of the second terminal surface 103, and then comprises a respective second portion of the at least one lateral element 104 which is diametrically opposite the second opening 20.

The surgical spacer device 100 comprises at least one hinge or pintle 107 configured for rotatably connecting the first half body 101a to the second half body 101b. In particular, the at least one hinge or pintle 107 is configured for a relative rotation of the first half body 101a with respect to the second half body 101b on at least one plane parallel to the first terminal surface 102 and/or to the second terminal surface 103. Preferably but non-limited thereto, the first half body 101a can freely rotate with respect to the second half body 101b of at least 180°.

The surgical spacer device 100 comprises a mechanical closure 108, configured for maintaining adjoined the first half body 101a and the second half body 101b, in order to a form the main body 101. In this preferred but non-limiting example, the mechanical closure 108 is in a position diametrically opposite with respect to the at least one hinge or pintle 107.

In this illustrative and non-limiting example, the mechanical closure 108 allows to hook the first half body 101a and the second half body 101b via a mechanical connection, wherein the half 101a is translated upwards and the pivot 109 placed on the upper end inside the seat 110 obtained on the half 101b is inserted. Once the pivot 109 is inserted in the seat 110, the half 101a is positioned aligned with the half 101b, and the pivot 109 of the half 101a is thus contained and blocked in the specific seat 110 of the half 101b.

FIG. 11 shows a prospective view of still another embodiment of a surgical spacer device 100, in open configuration.

In this illustrative and non-limiting example, the mechanical closure 108 allows to hook the first half body 101a and the second half body 101b via a different mechanical connection, wherein the half 101a is rotated and the elastic element 111 of the half 101b is inserted in the corresponding seat 112 obtained on the half 101a. Once the elastic elements 111 are inserted in the seat 112, the half 101a is positioned aligned with the half 101b and constrained thereto.

Figure 12:
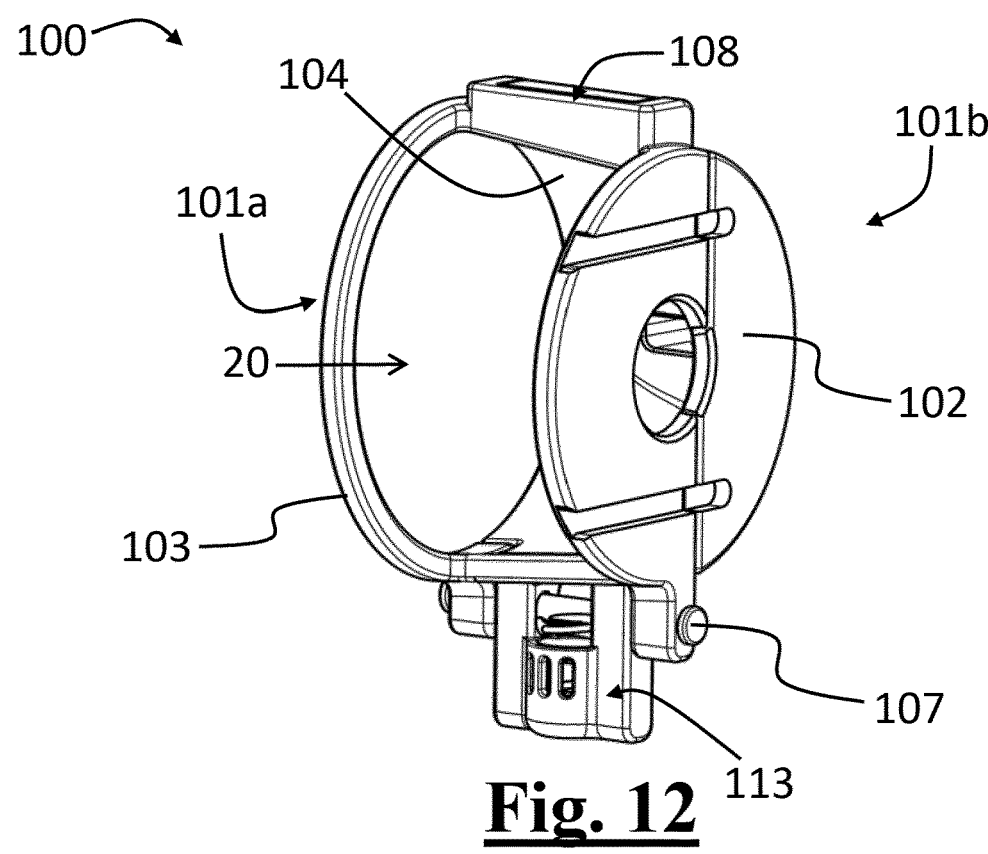
FIG. 12 shows a prospective view of still a further embodiment of a surgical spacer device according to the present invention, in closed configuration.
Figure 13:
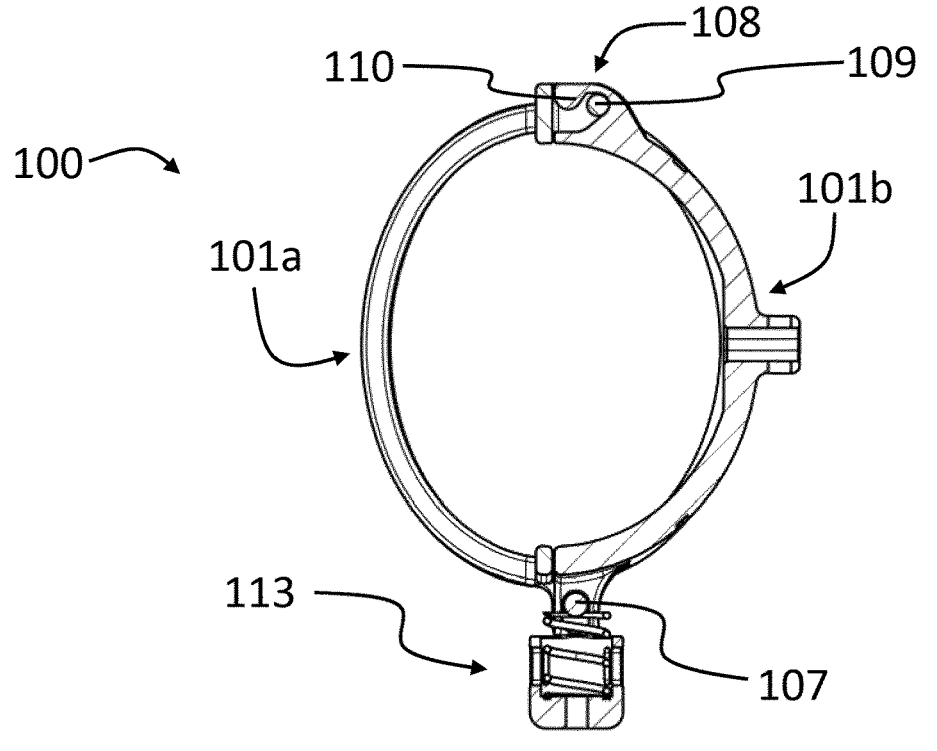
FIG. 13 shows a sectional view of the surgical spacer device of FIG. 12.

FIG. 12 shows a prospective view of still a further embodiment of a surgical spacer device 100 according to the present invention, in closed configuration, while FIG. 13 shows a sectional view of the surgical spacer device 100 of FIG. 12.

In this illustrative and non-limiting example, the mechanical closure 108 allows to hook the first half body 101a and the second half body 101*b*, via a mechanical connection comprising the pivot 109 and the seat 110 already described with reference to FIG. 10.

In addition, a spring clamping 113 is provided which helps constraining the first half body 101*a* and the second half body 101*b* in a stable manner, in order to build the main body 101.

The open configuration of the surgical spacer 100 ease the removal thereof from the joint 1, 2 once the surgery is finished and the glenoid implant is positioned, thus avoiding a possible obstruction of the surgical spacer device 100 by the glenoid implant, during the removal of the del surgical spacer device 100 from the joint.

Figure 14:
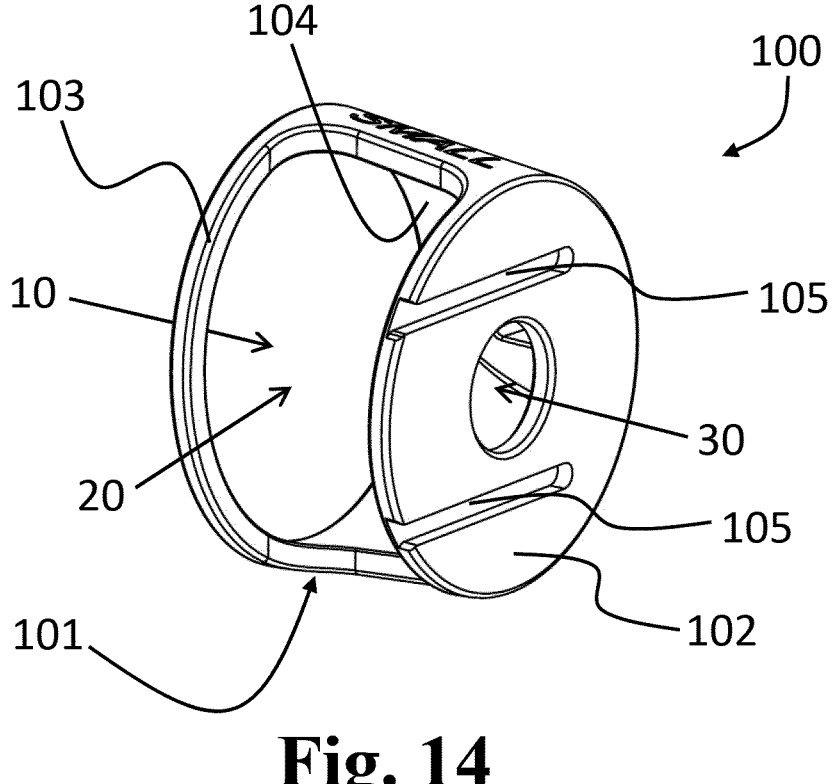
FIG. 14 shows a prospective view of a further embodiment of a surgical spacer device according to the present invention, made in a single piece.

FIG. 14 shows a prospective view of a further embodiment of a surgical spacer device 100, made in a single piece and thus not openable.

If no significant obstacles to the removal of the surgical spacer device 100 by the glenoid implantation occur, it is possible to provide a main body 101, substantially cylindrical or truncated-cone-shaped and internally hollow, made in a single piece.

In this embodiment as well, analogously to what has been already described, the main body 101 comprises, inter alia, the first terminal surface 102, the second terminal surface 103 and the at least one lateral element 104, which allow to build the structure of the surgical spacer device.

It is clear that further implementations and modifications of the present invention will be possible for those skilled in the art, in order to meet contingent needs. The above-described embodiments are therefore to be understood as provided for illustrative and non-limiting purpose.

For example, even if, in the described embodiments, the at least one lateral element 104 is represented by a single continuous lateral element, or in any case by continuous lateral elements belonging to the two half bodies 101*a* and 101*b*, in a variation, a plurality of lateral elements separated from each other could be used, for example columnar or anyway spaced apart elements, which form a cage-like structure or frame and in any case configured for maintaining a three-dimensional spaced structure of the main body 101.

What is claimed is:

1. A surgical spacer device for a shoulder joint, comprising:

a substantially cylindrical or truncated-cone-shaped main body, internally hollow and configured for insertion in a distracted shoulder joint, the main body comprising:

a plate (i) having a plate mating structure and (ii) defining a first flat terminal surface configured to abut a first bone portion of the shoulder joint;

an annular structure having a second terminal surface configured to abut a second bone portion of the shoulder joint that is opposite the first bone portion, the annular structure defining a first opening to aid in providing access to the second bone portion therethrough;

a lateral structure coupled to and extending between the plate and the annular structure such that a second opening is defined between the plate, the annular structure, and the lateral structure, the second opening being configured to allow lateral access into the main body and further into the second bone portion through first opening, the second opening circumferentially occupies an angular sector greater than 90 degrees; and a shim having a first shim mating structure, the shim configured to be coupled with the plate, via the first shim mating structure and the plate mating structure, thereby expanding the main body of the surgical spacer device, the shim having a second shim mating structure configured to be coupled with a second shim.

2. The surgical spacer device according to claim 1, wherein said first terminal surface and said second terminal surface are not parallel to each other, being sloped for partially reducing a thickness in height of said main body in a portion diametrically opposite said second opening, thus giving said main body a wedge shape so as to ease the insertion thereof in said distracted shoulder joint.

3. The surgical spacer device according to claim 1, wherein the first flat terminal surface includes a hole configured for passage of instruments or anchors extending from the first bone portion.

4. The surgical spacer device according to claim 1, wherein said main body is openable in a first half body and in a second half body, wherein said first half body comprises respective first portions of said first terminal surface and of said second terminal surface, and further comprises a respective first portion of said at least one lateral element including said second opening, and wherein said second half body comprises respective second portions of said first terminal surface and of said second terminal surface, and further comprises a respective second portion of said at least one lateral element diametrically opposite said second opening.

5. The surgical spacer device according to claim 4, comprising at least one hinge or pintle configured for rotatably connecting said first half body to said second half body.

6. The surgical spacer device according to claim 5, wherein said at least one hinge or pintle is configured for a relative rotation of said first half body and of said second half body with respect to at least one plane parallel to said first terminal surface and/or to said second terminal surface.

7. The surgical spacer device according to claim 5, further comprising a mechanical closure configured for maintaining adjoined said first half body and said second half body in order to form said main body.

8. The surgical spacer device according to claim 6, wherein said relative rotation is at least 180°.

9. The surgical spacer device according to claim 1, configured for insertion in a gleno-humeral distracted shoulder joint, wherein said first bone portion is humeral and said second bone portion is glenoidal, said first opening being sized to surround a glenoid cavity and to allow bone processing and implantation of prosthesis' glenoid components passing through said main body.

10. The surgical spacer device according to claim 1, wherein the shim has a thickness that expands the main body so as to increase a distraction quantity of the shoulder joint.

11. The surgical spacer device according to claim 10, wherein the first shim mating structure includes a pair of guide pins extending from a first side of the shim, and wherein the plate mating structure further comprises a pair of plate grooves configured to guide the pair of guide pins to couple the shim to the plate.

12. The surgical spacer device according to claim 11, wherein the pair of plate grooves are parallel to each other and the pair of guide pins are offset with respect to each other, being configured for sequentially engaging the pair of plate grooves.

13. The surgical spacer device according to claim 11, wherein each of the pair of plate grooves is open on one end thereof adjacent to the second opening of the at least one lateral element.

14. The surgical spacer device according to claim 10, wherein the shim comprises magnetic coupling means configured for maintaining a stable contact with the main body.

15. The surgical spacer device according to claim 10, wherein the shim is C-shaped with respective central cut-outs configured for surrounding instruments or anchors applied at the first terminal surface.

16. The surgical spacer device according to claim 1, wherein said main body further internally comprises hooking means on said at least one lateral element in a position opposite said second opening, said hooking means being configured for removably coupling with a handle for insertion in said distracted shoulder joint.

17. The surgical spacer device according to claim 1, wherein said at least one lateral element has a thickness and/or circumferential extension adapted to maintain said first terminal surface and said second terminal surface at a predetermined distance.

18. The surgical spacer device of claim 1, wherein the at least one lateral element includes a third opening accessible through the second opening, the third opening configured for removably coupling with a handle for insertion of the surgical spacer device into the distracted shoulder joint.

19. The surgical spacer device of claim 1, wherein the plate mating structure includes one or more grooves.

\* \* \* \* \*